United States Patent [19]

Allen et al.

[11] Patent Number: 5,144,053

[45] Date of Patent: Sep. 1, 1992

[54] ALUMINUM ALKYLS AND LINEAR 1-OLEFINS FROM INTERNAL OLEFINS

[75] Inventors: Robert H. Allen; Keith G. Anderson; Steven P. Diefenbach; Ronny W. Lin; Larry H. Nemec; Andrew D. Overstreet; Gene C. Robinson, all of Baton Rouge, La.

[73] Assignee: Ethyl Corporation, Richmond, Va.

[21] Appl. No.: 804,039

[22] Filed: Dec. 9, 1991

Related U.S. Application Data

[62] Division of Ser. No. 674,104, Mar. 25, 1991.

[51] Int. Cl.$^5$ .............................................. C07F 5/06
[52] U.S. Cl. ................................. 556/190; 556/170; 556/187; 585/637; 585/664; 585/670; 585/671
[58] Field of Search .................... 556/170, 187, 190; 585/637, 664, 671, 670

[56] References Cited

U.S. PATENT DOCUMENTS

| | | | |
|---|---|---|---|
| 2,959,607 | 11/1960 | Werber et al. | 260/448 |
| 2,962,513 | 11/1960 | Meiners et al. | 260/448 |
| 2,978,523 | 4/1961 | Coyne et al. | 260/683.15 |
| 3,065,281 | 11/1962 | Hall et al. | 260/669 |
| 3,322,806 | 5/1967 | Asinger et al. | 260/448 |
| 3,352,894 | 11/1967 | Crain et al. | 260/448 |
| 3,369,037 | 2/1968 | Johnston | 260/448 |
| 3,384,677 | 5/1968 | Franz et al. | 260/683.2 |
| 3,489,731 | 1/1970 | Imoto et al. | 260/80.78 |
| 3,509,228 | 4/1970 | Franz et al. | 260/683.2 |
| 3,641,184 | 2/1972 | Smith et al. | 260/683.2 |
| 3,657,299 | 4/1972 | Ichiki et al. | 260/448 A |
| 4,314,090 | 2/1982 | Shewbart et al. | 585/328 |
| 4,380,684 | 4/1983 | Fowler et al. | 585/328 |
| 4,455,289 | 6/1984 | Poe et al. | 423/630 |
| 4,484,016 | 11/1984 | Maschmeyer et al. | 585/510 |
| 4,918,254 | 4/1990 | Diefenbach et al. | 585/328 |

FOREIGN PATENT DOCUMENTS 1329140  9/1973  United Kingdom .

OTHER PUBLICATIONS

Chemische Berichte 97, pp. 2515-2520 (1964), Asinger, et al.
German Thesis, Rainer Oberghaus, Technishen Hochschelle, pp. 1-108, Aachen (1969).
Chem. Berg. 104, pp. 1332-1334 (1871).

*Primary Examiner*—Jose G. Dess
*Assistant Examiner*—Porfirio Nazario
*Attorney, Agent, or Firm*—David M. Bunnell

[57] ABSTRACT

Linear 1-olefins are prepared from internal olefins by (i) reacting them in the presence of an isomerization catalyst and a tri-lower alkyl aluminum so as to cause internal olefin to isomerize to 1-olefins which displace the lower alkyl groups to form a trialkyl aluminum compound in which at least one of the alkyl groups is a linear alkyl derived from the 1-olefin, and, thereafter, (ii) reacting the trialkyl aluminum compound with a 1-olefin so as to displace the linear alkyl from the trialkyl aluminum compound, thereby forming a linear 1-olefin product which is substantially free of internal olefins.

12 Claims, No Drawings

ALUMINUM ALKYLS AND LINEAR 1-OLEFINS FROM INTERNAL OLEFINS

This application is a division of application Ser. No. 674,104, filed Mar. 25, 1991.

BACKGROUND

This invention relates generally to the isomerization of internal olefins and more specifically to the preparation of aluminum alkyls from internal olefins and the recovery of linear 1-olefin compounds from the aluminum alkyls.

Linear 1-olefin compounds such as 1-hexene are useful comonomers with lower olefins to prepare polymers having improved physical properties. The 1-hexene is normally produced as a by-product of olefin production by a variety of well-known processes such as the ethylene chain growth process in which ethylene reacts with lower aluminum alkyls to form higher alkyl aluminum compounds. The higher, $C_4$ to $C_{30}$ or above, alkyl groups are then displaced from the aluminum by, for example, ethylene or butene to form $C_4$ to $C_{30}$ linear 1-olefins which can be separated and recovered. Increasing demand for 1-hexene has produced a need for preparing it as the primary product. Processes for preparing olefins such as by the dehydrogenation of paraffins or the metathesis of other olefins produce mainly internal olefin products which must then be converted to 1-olefins. Asinger et al. U.S. Pat. No. 3,322,806 describe the preparation of primary alcohols from internal olefins by reacting a non-1-olefin with an aluminum lower alkyl in the presence of catalysts which are compounds of zirconium, uranium, vanadium, chromium, thorium, tungsten, and titanium. The catalyst is believed to promote the conversion of internal olefins to 1-olefins which displace the lower alkyl groups of the aluminum alkyl. The aluminum alkyl is then converted to a primary alcohol by oxidation and hydrolysis. Asinger et al. also disclose such an isomerization/displacement process to prepare alcohols in Chemische Berichte 97, pages 2515-2520 (1964). They reported that nickel compounds were inactive. Later, the thesis of Rainer Oberghaus, Technishen Hochschulle, Aachen, (1969) reported a 55 percent yield of a 1-alcohol from i-$Bu_2$AlR formed by reacting internal olefin and triisobutylaluminum using a nickel(II) acetylacetonate catalyst.

BRIEF SUMMARY

In accordance with this invention there is provided a process for making an alkyl aluminum compound from an internal olefin, said process comprising: reacting (i) a linear internal olefin containing 4 to about 30 carbon atoms or a mixture of such internal olefins, and (ii) a trialkyl aluminum which contains less than about 1.0 wt% of aluminum hydride impurity, the mole ratio of said linear internal olefins to said trialkyl aluminum being about 1–40:1, in the presence of a catalytic amount of a nickel-containing isomerization/displacement catalyst to cause isomerization of the internal olefinic double bond to form at least some linear 1-olefin and to cause the linear 1-olefin so-formed to displace alkyl groups from said trialkyl aluminum and form an alkyl aluminum compound wherein at least one of the alkyl groups bound to aluminum is a linear alkyl derived from said linear 1-olefin.

In another aspect of the invention there is provided a process for making a linear 1-olefin compound from an internal olefin, said process comprising:

(a) reacting (i) a linear internal olefin containing 4 to about 30 carbon atoms or a mixture of such internal olefins, and (ii) a trialkyl aluminum, the mole ratio of said linear internal olefins to said trialkyl aluminum being about 1–40:1, in the presence of a catalytic amount of an isomerization catalyst to cause isomerization of the internal olefinic double bond to form at least some linear 1-olefin which displaces alkyl groups from said trialkyl aluminum and forms an alkyl aluminum compound wherein at least one of the alkyl groups bound to aluminum is a linear alkyl derived from said linear 1-olefin, and thereafter, (b) reacting said alkyl aluminum compound with a 1-olefin so as to displace said linear alkyl from said alkyl aluminum compound and form a free linear 1-olefin compound.

DETAILED DESCRIPTION

The internal olefins which are isomerized in accordance with this invention contain from 4 to about 30 carbon atoms, preferably 4 to 18 carbon atoms and can include mixtures of such olefins. Such internal olefins can be obtained from a number of sources as known in the art. For example, by the dehydration of alcohols or alcohol mixtures, by the metathesis or disproportionation of olefins such as n-butene to form ethylene and hexenes or mixtures of olefins such as ethylene and n-octene to form butenes and hexenes, or by the dehydrogenation of $C_4$-$C_{30}$ normal paraffins. Suitable internal olefins include, for example, cis and trans-2-hexene, cis and trans-3-hexene, mixed internal hexenes, mixed internal dodecenes, mixed internal octadecenes and the like.

The alkylaluminum compounds for the isomerization/displacement process have alkyl groups which, preferably, contain fewer carbons than the predominant carbon number of the internal olefins. In any event, the displaced olefin from the alkylaluminum compound should usually have a boiling point below the isomerized olefin because removal of the displaced olefin drives the reaction. However, it is also possible that the displaced olefin can be a vinylidene olefin, in which case thermodynamic equilibria rather than removal of the olefin can drive the reaction. Suitable alkylaluminum compound-s which contain alkyl groups having from 2 to about 20 carbon atoms, preferably 2 to 12 carbon atoms, include, for example, triethylaluminum, tri-n-propylaluminum, tri-n-butylaluminum, triisobutylaluminum, trineohexylaluminum, tri-n-octylaluminum, tri-n-dodecylaluminum, tri-n-octadecylaluminum and the like. Preferred compounds are straight chain alkyl compounds and especially those where the alkyl group does not isomerize upon displacement such as tri-n-propyl aluminum such that the displaced olefin can be easily recycled. We have found that low hydride content aluminum alkyl compounds (less than about 1.0 wt % and preferably less than about 0.1 wt %) are required to achieve good yields when using nickel catalysts, because the presence of aluminum hydride impurities rapidly deactivates the catalyst. The $AlH_3$ or $R_2AlH$ content can be reduced by contacting the aluminum alkyl with a 1-olefin such as propylene.

Suitable catalysts for isomerization of the internal olefins include, for example, alkali metals such Na or Li on $Al_2O_3$; Pd, Ni, or Pt on inert supports such as carbon; La on SiO$_2$-Al$_2$O$_3$; cobalt halide-ligand complexes, e.g. CoBr$_2$.2P(cyclohexyl)$_3$, metal oxides, metal amides, and the like. Preferred catalysts are those which catalyze both isomerization and displacement, for example, titanium and zirconium compounds such as Ti(OBu)$_4$ and Zr(OBu)$_4$, and the like. Especially preferred are nickel containing compounds which, surprisingly in view of the teachings of Asinger et al., have been found to be very effective isomerization/displacement catalysts which provide yields of aluminum alkyls from internal olefins of about 60 to 90% or more. Such nickel compounds include, for example, nickel(II) salts; nickel-(II) carboxylates, nickel(II) acetonates and nickel(0) complexes. Examples of nickel(II) salts include nickel halides, e.g., nickel chloride, nickel bromide, nickel iodide, and their hydrates and the like. Also useful are nickel(II) oxide, nickel(II) hydroxide and the like.

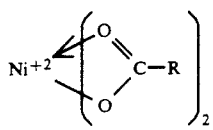

where R is hydrogen or C$_1$-C$_{16}$ alkyl; aryl, i.e. phenyl, naphthyl; substituted aryl, i.e. phenyl and naphthyl substituted with one or more of C$_1$-C$_{16}$ alkyl, halogen (Cl, Br, I, F), and/or haloalkyl etc; aralkyl, i.e. benzyl, naphthobenzyl; and substituted arylalkyl where the aryl group is substituted as described above for substituted aryl, and the like.

Examples of nickel carboxylates include nickel acetate, nickel 2-ethylhexanoate and nickel naphthenate.

Nickel acetonates such as acetylacetonate can be represented by the formula:

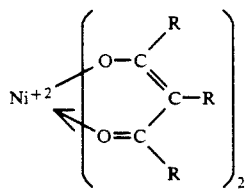

when R is as defined above for the nickel carboxylates.

The foregoing three types of Ni(II) catalysts are believed to be reduced to Ni(0) compounds in the presence of aluminum alkyl/olefin mixtures and form complexes with the olefin which catalyze the isomerization-displacement reaction.

Examples of Ni(0) complex catalysts include Ni(0) olefin complexes such as Ni(CO)$_4$, nickel bis-1,5-cyclooctadiene (Ni(COD)$_2$), Ni(C$_2$H$_4$)$_3$, Ni(norbornene)$_3$, nickel cyclododecatriene and the like. Other Ni(0) catalysts are nickel compounds which are complexed with a ligand such as a trivalent phosphorous compound. The ligand acts to improve the storage stability of catalysts such as Ni(COD)$_2$.

Examples of specific ligand compounds include triphenylphosphine, triethylphosphine, triethoxyphosphine, cyclohexylphosphine, P(SiMe$_3$)$_3$, and the like.

Examples of specific Ni catalyst-ligand complexes include Ni(PPh$_3$)$_4$, Ni(PEt$_3$)$_4$ and Ni(P(OEt)$_3$)$_4$, each of which are commercially available, and Ni(Me$_2$PCH$_2$)$_2$, Ni(P(SiMe$_3$)$_3$)$_3$, Ni(COD)$_2$.(cy$_2$PCH$_2$)$_2$ (where cy=cyclohexyl), Ni(COD)$_2$.(Me$_2$PCH$_2$)$_2$, Ni(COD)$_2$.P(O-o-tolyl)$_3$ with Ni(COD)$_2$.Pcy$_3$ being preferred. The catalyst complexes can be formed by mixing the nickel compound such as Ni(COD)$_2$ with the desired phosphine in a P/Ni mole ratio of at least 2 for monodentate phosphines at least 1 for the bidentate phosphine ligands. Most nickel(0) phosphine ligands are prepared by reduction of a nickel(II) salt in the presence of a phosphine ligand or by mixing the phosphine with a nickel-olefin complex.

Mixtures of any of the above mentioned catalysts can also be used. Separate catalysts can be used for isomerization and displacement provided that they do not interfere with each other. Examples of displacement catalysts include, for example, colloidal Ni, Pt, Co, nickel acetylacetonate, cobalt carboxylates, e.g. cobalt naphthenate or cobalt acetate, nickel carboxylates, e.g. nickel naphthenate and the like.

The mole ratio of internal olefin to-tri-alkylaluminum can vary and preferably ranges from about 1–40:1 with 5–15:1 preferred and about 10:1 most preferred. Catalytic amounts of nickel catalyst which are effective in the isomerization/displacement process generally range from about 0.01 to 5.0 mole percent of the tri-lower alkyl aluminum and preferably about 0.02 to 1.0 mole percent.

According to the isomerization/displacement process, the catalyst is preferably first mixed with the internal olefins and this mixture is added to the trialkyl aluminum. Alternatively the catalyst can be added to a mixture of trialkyl aluminum and internal olefin. Both isomerization and displacement can be simultaneously carried out in the same vessel but the isomerization reaction can be initiated in a first reactor and then fed to a second reactor containing the trialkyl aluminum. The reaction can be carried on in a batch or continuous manner. In order to favor the replacement of the alkyl groups by the isomerized olefins, the displaced alkyl groups in the form of their corresponding 1-olefins can be removed as vapor from the reaction mixture and in one embodiment of the invention are used in the recovery of isomerized 1-olefins by back-displacement. Unreacted internal olefins can be separated from the reaction mixture, such as by distillation or vacuum stripping and returned to the isomerization/displacement reaction. Suitable reaction temperatures range from about −20° to 200° C., preferably about 30° to 100° C. Suitable reaction pressures range from about 0 to 100 psia, preferably about 1 to 45 psia and reaction times usually range from about 0.1 to 2 hours. The use of solvents is not necessary but inert aliphatic and aromatic hydrocarbons of the proper boiling point for the desired reaction temperature can be used. It is sometimes advantageous, and especially when using a reactor in which distillation takes place concomitantly with the isomerization/displacement reaction, to include an inert diluent such as isoheptane, heptane, octane, isooctane , etc. in the feed to provide boil up in the bottom of the reactor without excessive bottoms temperatures which cause decomposition of the aluminum alkyls.

According to the embodiment of the process of the invention for preparing linear 1-olefins, the n-alkyl groups from the isomerized internal olefins are back-displaced from the trialkyl aluminum compounds formed in the isomerization/displacement reaction. A suitable displacement process is described, for example, in U.S. Pat. No. 4,918,254 whose teachings are incorporated herein by reference.

As described above, the displaced 1-olefin recovered from the isomerization/displacement reaction can preferably be used as the olefin to back-displace the linear 1-olefin from the aluminum alkyl. The regenerated trialkyl aluminum can then be recycled to the isomerization/displacement reaction. However, a different olefin can be used for back-displacement and 1-olefins having from 2 to about 18 carbon atoms including mixtures thereof are especially suitable. The back-displacement can be accomplished without a catalyst but is preferably carried out in the presence of a displacement catalyst. We have discovered that the nickel catalysts which are carried over from the isomerization/displacement step are effective to catalyze the back-displacement even though they have become inactive in catalyzing the isomerization/displacement reaction. The catalysts are apparently reactivated in the presence of the displacing olefin and heat, for example temperatures above about 40° C. and, preferably 40°–80° C. Fresh catalysts can also be added. Preferred catalysts should not have any significant isomerization activity under the conditions used and include, for example, cobalt carboxylates such as cobalt naphthenate and the like. Nickel complexes, for example, nickel acetylacetonate, nickel carboxylates such as nickel naphthenate, and nickel acetate, are suitable if used in combination with Pb to prevent isomerization. Cyclodienes and acetylene hydrocarbons, such as phenyl acetylene, can also be used in the displacement reaction to suppress isomerization activity and prolong catalyst life. Effective amounts of catalyst depend upon the catalyst used. Generally amounts of from about 1 to 100 parts per million based on the weight of the reaction mixture can be used and, preferably about 5–50 ppm. Reaction temperatures of from about $-10°$ to 200° C. are suitable for catalyzed displacement. The aluminum alkyl feed to be back-displacement can be treated with a 1-olefin to remove any aluminum hydride so as to extend catalyst life. Higher temperatures of about 300° C. or above may be needed for thermal displacement without catalysts.

The amount of 1-olefin fed to the displacement reaction should be in stoichiometric excess over the amount required to replace all alkyl groups. Preferably the amount of 1-olefin should be at least a 200 percent excess over the stoichiometric amount required to replace all alkyl groups. Still more preferably the 1-olefin feed should be at least a 500 percent stoichiometric excess over the trialkyl aluminum feed stream. In this manner, since the displacement reaction is an equilibrium reaction, the alkyl substitution in the trialkyl aluminum product will more closely approach the distribution of the 1-olefin feed.

Both displacement and side reactions (e.g. isomerization, dimerization, chain growth) proceed concurrently. However, the displacement reaction rate is much higher than the rate of the side reactions. This permits termination of the displacement reaction after a time that allows it to go substantially toward the equilibrium conversion and before a time in which the side reactions, especially isomerization, become significant. By "significant" is meant the amount of undesired by-products which would render the olefin effluent stream unsuitable for its intended purpose. In general, the 1-olefin product should contain less than 25 weight percent newly formed combined internal, tri-substituted and vinylidene olefins. The preferred 1-olefin product is at least 80 weight percent vinyl 1-olefin and more preferably at least 90 weight percent vinyl 1-olefin based on the tri-n-alkylaluminum converted. The process is capable of making 1-olefin product that is over 97 weight percent vinyl 1-olefin based on tri-n-alkylaluminum converted.

Since all rates vary with temperature and amount of catalyst, the optimum time for termination under each specific condition will require a minimal amount of experimentation. In general when operating at 25° C., the reaction should be terminated after a reaction period of about 30 seconds to 1 hour. A preferred reaction time is 1–20 minutes and most preferred 1.75–2.25 minutes. At higher temperatures, e.g. 50°–100° C., the preferred reaction time before side reactions become significant will be shorter.

In using a nickel displacement catalyst, when the displacement has proceeded to the desired extent, usually close to reaction equilibrium, a catalyst poison can be added in an amount that will deactivate the nickel catalyst and prevent undesirable side reactions. These poisons include lead and copper and compounds thereof. Suitable lead compounds are lead naphthenate, lead acetylacetonate, lead 2-ethylhexanoate, tetraethyl lead, etc. Suitable copper compounds are copper naphthenate, copper acetylacetonate, cuprous bromide, cuprous 2-ethylhexanoate and the like. Use of the metals as the catalyst poison requires the metals to be in very finely divided forms and requires a greater amount of the catalyst poison. For example, amorphous lead metal was an effective catalyst poison at a Pb/Ni atom ratio of about 500. The catalyst poisons which are effective at the lowest concentrations have been lead compounds, e.g. lead naphthenate, lead 2-ethylhexanoate and lead acetylacetonate.

The amount of catalyst poison should be an amount that effectively inhibits all undesired side reactions. With lead compounds a lead/nickel atom ratio of 1.0 has been effective and even lower amounts may be effective. Hence a useful Pb/Ni atom ratio is about 0.5/1.0 to 5.0/1.0.

After the catalyst poison has been added, the trialkyl aluminum product can be recovered by conventional methods such as distillations. When lead compounds are used as the poison, nickel and at least part of the lead form a precipitate which can be removed by filtration.

Isomerization during back-displacement can also be suppressed by the addition of an isomerization suppressing amount, preferably, from about 1.0 to 5.0 grams per milligram of nickel in the catalyst, of a cyclodiene compound such as a cyclooctadiene, cycloheptatriene or 1,3-cyclohexadiene and, preferably 1,5-cyclooctadiene. Although small amounts of such cyclodienes favor isomerization, the use of at least about 1.0 gram of cyclodiene per milligram of nickel in the back-displacement reaction, produces a vinyl olefin product which has a reduced isomer impurity content. Unlike lead, the cyclo-octadiene can be easily recovered for reuse. This avoids the need to remove added lead and inactivated nickel catalyst by filtration prior to recycling the aluminum alkyl to the isomerization/displacement reaction. Isomerization is also suppressed by acetylenic compounds.

The invention is further illustrated by, but is not intended to be limited to, the following examples.

Catalyst Preparation

C-1

$Ni(COD)_2 \cdot Pcy_3$ are prepared by dissolving known amounts of $Ni(COD)_2$ and $Pcy_3$ (mole ratios of phosphine to Ni of about 2:1 to 5:1) in 10 mL of dry heptane to give about $10^{-2}$ molar solutions. The solutions are stored in a drybox. Portions are removed in a 2.0 mL gastight syringe for addition to the reaction mixture.

C-2

A known amount of Ni(II) naphthenate (7.33 wt % Ni) is dissolved in 10 mL of dry heptane to give about $10^{-3}$ gram Ni/mL solutions. Portions are placed in a 2.0 mL gastight syringe for addition to the reaction mixture.

C-3

$Ni(OAc)_2 4H_2O$ (1.0 gram) is dried and dissolved in glacial acetic acid to give about a 0.02 g Ni/mL solution. This solution (e.g. 16 microliter) is added by syringe to the reaction mixture over a period of 30 minutes.

C-4

Known amounts of commercially available catalysts such as $Ni(COD)_2$, $Ni(PPh_3)_4$ and $Ni(P(OEt)_3)_4$ to give desired concentrations are dissolved in 1-2 mL of a mixture of internal hexenes and added by syringe to the reaction mixture. The $Ni(COD)_2$ is recrystallized from pentene before use.

C-5

Catalyst solutions of $Ni(COD)_2$ + phosphine ligands, for example, $P(O-o-tolyl)_3$, $P(SiMe_3)_3$, $Me_2PCH_2CH_2PMe_2$, and $cy_2PCH_2CH_2Pcy_2$ (where cy=cyclohexyl) are prepared by dissolving $Ni(COD)_2$ in olefin or heptane and then adding the desired amount (mole ratios of phosphine to Ni of about 2:1 to 5:1) of phosphine ligand. The resulting solutions are added by syringe to the reaction mixture.

Aluminum Alkyl Preparation

Triethylaluminum (TEA), Tributylaluminum (TNBA) and Tri-n-propylaluminum (TNPA) are treated to reduce the aluminum hydride ($R_2AlH$) content by contact with propylene (20-30 mL $R_3Al$, 150 psi propylene, 12 hours at 60° C.). The aluminum hydride content can also be reduced by refluxing with 1-hexene at 70° C. for 2 hours after which the 1-hexene is vacuum stripped.

Internal Olefin

Individual $C_6$ olefin isomers are commercially available. Isomerized internal hexenes are prepared by isomerizing 1-hexene with a $Ni(COD)_2 \cdot TNHA$ catalyst. A typical wt % composition of the resulting isomers is 1.2% 1-hexene, 23.3% c,t-3-hexene, 59.8% t-2-hexene, and 15.7% c-2-hexene. The olefins are stored over activated (140° C., 1 mm, 18 hours) Kaiser A2 alumina in a separatory funnel for at least 3 hours then are slowly passed through the alumina under nitrogen and stored in the dry box.

General Isomerization — Displacement Procedure $R_3Al$ (~15 m moles) is placed into an 8 dram vial. Dry cyclooctane is added to the $R_3Al$ as an internal standard. The amount of cyclooctane in grams is equal to the theoretical amount in grams of hexane formed after hydrolysis at 100% conversion to tri-n-hexylaluminum (TNHA). About 160 m moles (19-20 mL) of internal olefin are measured into a graduated cylinder then added to the $R_3Al$/cyclooctane mixture. The $R_3Al$/olefin/cyclooctane mixture is placed into a 25 mL pressure equalized addition funnel. The funnel is removed from the dry box and placed into a 3-neck 50-mL flask equipped with a stir bar, thermometer, and reflux-cold finger head connected to a dry ice trap. The reflux-cold finger head consists of a 10 mm length cold finger above a 15 mm length Vigreaux column. The cold finger is maintained at 5° C. Nitrogen is slowly flushed through the apparatus and into a mineral oil bubbler. After adding the mixture to the flask, the addition funnel is replaced with a wired down septum. The mixture is heated to vigorous reflux (~67° C.) to disengage olefin which forms by displacement of the R group of the starting $R_3Al$ compound (i.e. for TNPA, R = propylene). The nickel catalyst solution is then added to the mixture via syringe through the septum over typically 2-3 minutes. The reaction mixture is kept at reflux. Aliquots (0.2 mL) of the mixture are removed periodically under $N_2$ with a 2.0 mL pressure Lok gastight syringe and hydrolyzed in aqueous HCl (3.0 mL/nonane 0.7 mL). After about 2 hours the mixture is cooled to room temperature. The hydrolyzed aliquots are analyzed by gas chromatography and Carbon 13 - NMR to determine the yield of tri-n-hexylaluminum. In some examples as noted, where increased amounts of reactants were used in order to provide sufficient TNHA product for back-displacement, a larger reaction flask (300 mL) was used.

EXAMPLE 1

An internal hexenes/TneoHA (trineohexyl aluminum) mixture of mole ratio 10 was boiled under reflux. A $Ni(COD)_2 \cdot Pcy_3$ in heptane catalyst solution was added over 1-2 minutes to give a nickel concentration of 21 ppm (based on total reaction mass). Percent conversion to TNHA over time as determined by G. C. was as follows:

| Time (min.) | % TNHA |
| --- | --- |
| <5 | 21.4 |
| 5 | 22.0 |
| 10 | 22.4 |
| 15 | 23.1 |
| 30 | 23.2 |
| 60 | 21.8 |

EXAMPLE 2

A trans-2-hexene/TEA (triethylaluminum) mixture of mole ratio 11.6 was boiled under reflux. A $Ni(COD)_2$ in trans-2-hexene catalyst solution was added over 1-2 minutes to give a nickel concentration of 1385 ppm. Percent conversion to TNHA over time as determined by gas chromatography was as follows:

| Time (min.) | % TNHA |
| --- | --- |
| 20 | 23.2 |
| 60 | 36.3 |
| 110 | 43.4 |

EXAMPLE 3

A Fisher Porter glass pressure vessel was charged with an internal hexenes/TIBA (trisobutylaluminum) mixture of mole ratio 11.3 and a $Ni(COD)_2 \cdot Pcy_3$ catalyst in heptane (25 ppm nickel concentration). The vessel was placed into a preheated oil bath at 69° C. Aliquots were periodically removed, hydrolyzed, and analyzed by gas chromatography. Percent conversion to TNHA over time was as follows:

| Time (min.) | % TNHA |
| --- | --- |
| 2.5 | 14.6 |
| 10 | 46.9 |
| 15 | 59.4 |
| 30 | 69.8 |
| 50 | 70.8 |
| 110 | 71.9 |

EXAMPLE 4

A trans-3-hexene/TNBA (tri-n-butylaluminum) mixture of mole ratio 9.8 was boiled under reflux. A Ni(COD)$_2$ catalyst in trans-3-hexene solution was added over 2-3 min to give a nickel concentration of 1400 ppm. Percent conversion to TNHA over time as determined from gas chromatography was as follows:

| Time (min.) | % TNHA |
| --- | --- |
| 7 | 50.6 |
| 20 | 77.4 |
| 34 | 83.5 |
| 90 | 86.8 |
| 120 | 85.7 |

EXAMPLE 5

An internal hexenes/TNPA (tri-n-propylaluminum) mixture of mole ratio 10 was boiled under reflux. A Ni(COD)$_2$ catalyst in internal hexenes was added over 2 minutes to give a nickel concentration of 68 ppm. Percent conversion to TNHA over time as determined by gas chromatography was as follows:

| Time (min.) | % TNHA |
| --- | --- |
| 7 | 53 |
| 15 | 72 |
| 23 | 80 |
| 38 | 82 |
| 105 | 81 |
| 135 | 82 |

EXAMPLE 6

An internal hexenes/TNPA (tri-n-propylaluminum) mixture of mole ratio of 10 was boiled under reflux, A Ni(COD)$_2$.Pcy$_3$ catalyst in heptane was added over 1-2 min to give a nickel concentration of 30 ppm. Percent conversion to TNHA over time as determined by gas chromatography was as follows:

| Time (min.) | % TNHA |
| --- | --- |
| 4 | 43 |
| 8 | 66.7 |
| 15 | 78.2 |
| 30 | 87.3 |
| 60 | 85.2 |
| 90 | 91.0 |
| 120 | 88.2 |

EXAMPLE 7

An internal hexenes/TNPA (tri-n-propylaluminum) mixture of mole ratio 10 was boiled under reflux. A Ni(II) acetate catalyst in acetic acid (Catalyst Solutions, Example C-3) was added to give a nickel concentration of 20 ppm. Percent conversion to TNHA over time as determined by gas chromatography was as follows:

| Time (min.)[1] | % TNHA |
| --- | --- |
| 5 | 77.6 |
| 10 | 81.8 |
| 15 | 81.7 |
| 30 | 85.2 |
| 60 | 86.8 |
| 100 | 85.3 |

[1] Time after catalyst was fed.

EXAMPLE 8

An internal hexenes/TNPA (tri-n-propylaluminum) mixture, 1125 m mole internal hexenes and 108 m mole TNPA, which was treated with 1-hexene by refluxing at atmospheric pressure to remove hydride and isobutyl impurities, was boiled under reflux using Ni(II) acetate catalyst (20 ppm Ni, 2.24 mg) which was added over about 27 minutes. The reaction temperature ranged from about 62°-69° C. and the reaction was continued 120 minutes and the mixture was then vacuum stripped. The percent conversion of TNPA to TNHA over time as determined by gas chromatography was as follows:

| Time (min.)[1] | % TNHA |
| --- | --- |
| 5 | 81.1 |
| 15 | 87.6 |
| 30 | 91.5 |
| 60 | 95.4 |
| 120 | 97.6 |

[1] Time after catalyst was fed.

EXAMPLE 9

An internal hexenes/TNPA (tri-n-propylaluminum) (treated with propylene) mixture of mole ratio 10 was boiled under reflux. A nickel(II) naphthenate catalyst (0.8 mg Ni) was added over about 16 minutes along with 5.9 mg of 1,5-cyclooctadiene co-catalyst. The temperature ranged from about 71°-79° C. The conversion or TNPA to TNHA over time as determined by gas chromatography was as follows:

| Time (min.)[1] | % TNHA |
| --- | --- |
| 5 | 70.0 |
| 10 | 77.8 |
| 15 | 78.2 |
| 30 | 86.2 |
| 60 | 89.8 |
| 100 | 90.4 |

[1] Time after catalyst was fed.

EXAMPLE 10

An internal hexenes/TNPA (tri-n-propylaluminum) mixture of mole ratio 10 was added to a 50 cc flask containing 0.5 mg (25 ppm Ni) of a nickel(II) chloride powder catalyst, which was obtained by oven drying NiCl$_2$.6H$_2$O using a N$_2$ purge. The reaction temperature ranged from about 20° to 76° C. The conversion of TNPA to TNHA over time as determined by gas chromatography was as follows:

| Time (min.) | % TNHA |
| --- | --- |
| 5 | 9.9 |
| 10 | 27.0 |
| 15 | 44.0 |
| 30 | 60.8 |
| 60 | 67.7 |
| 100 | 71.8 |

EXAMPLE 11

An internal hexenes/TNPA (tri-n-propylaluminum) mixture, 1607 m mole internal hexenes and 192 m mole of TNPA which was treated with propene (but still had 0.18 wt % iso-butyl impurity) was boiled under reflux in a 300 mL flask using a first portion of nickel(II) acetate catalyst (24ppm Ni), which was added over about 30 minutes. After 30 minutes reaction, additional catalyst (12 ppm Ni) was fed over 5 minutes. The reaction temperature ranged from about 57°-70° C. The percent conversion of TNPA to TNHA over time as determined by gas chromatography was as follows:

| Time (min.)[1] | % TNHA |
| --- | --- |
| 5 | 43.2 |
| 15 | 51.4 |
| 30 | 60.0 |
| 60 | 71.9 |
| 120 | 75.6 |
| | 91.5[2] |

[1]Time after the first portion of catalyst was fed.
[2]Based on the sample of the product which was vacuum stripped to remove the excess n-hexenes.

EXAMPLE 12A

An internal hexenes/TNPA (tri-n-propylaluminum) mixture, 1190 m mole internal hexenes and 27.4 grams of the TNPA solution (from Example 11B) containing about 33.4 m mole of TNPA, was boiled under reflux in a 300 mL flask initially using a first portion of nickel(II) acetate catalyst (15 ppm Ni) which was added over about 33 minutes. Additional catalyst (15 ppm Ni as nickel(II) acetate) was then added over about 5 minutes. The reaction temperature ranged from about 70°-72° C. The percent conversion of TNPA to TNHA over time as determined by gas chromatography was as follows:

| Time (min.)[1] | % TNHA |
| --- | --- |
| 5 | 33.6 |
| 15 | 30.9 |
| 30 | 36.6 |
| 60 | 42.1 |
| 150 | 57.4 |

[1]Time after the first portion of catalyst was fed.

The product was vacuum stripped to remove excess n-hexenes.

EXAMPLE 13A

An internal hexenes/TNPA (tri-n-propylaluminum) mixture, 1005 m mole internal hexenes and 96 m mole of TNPA was boiled under reflux in a 300 mL flask using a nickel(II) acetate catalyst (2mg, 20ppm Ni) which was added over 33 minutes. The reaction temperature ranged from about 66°-69° C. The percent conversion of TNPA to TNHA over time as determined by gas chromatography was as follows:

| Time (min.)[1] | % TNHA |
| --- | --- |
| 5 | 67.5 |
| 15 | 75.1 |
| 30 | 80.8 |
| 60 | 88.2 |
| 120 | 94.0 |

[1]Time after catalyst was fed.

The product was vacuum stripped to remove excess hexenes.

EXAMPLE 14A

An internal hexenes/TNPA (tri-n-propylaluminum) mixture, 1005 m mole internal hexenes and 96 m mole of TNPA was boiled under reflux in a 300 mL flask using a nickel(II) acetate catalyst (2 mg, 20 ppm Ni) added over 32 minutes. After 30 minutes reaction, an additional portion of this catalyst (1 mg Ni) was added in about 2 minutes. The reaction temperature ranged from about 64°-69° C. The percent conversion of TNPA to TNHA over time as determined by gas chromatography was as follows:

| Time (min.)[1] | % TNHA |
| --- | --- |
| 5 | 32.6 |
| 15 | 42.2 |
| 30 | 54.2 |
| 60 | 73.9 |
| 150 | 91.4 |

[1]Time after the first portion of catalyst was fed.
The product was vacuum stripped to remove excess hexenes.

EXAMPLE 15A

An internal hexenes/TNPA (tri-n-propylaluminum) mixture, 964 m mole internal hexenes and 123 m mole of TNPA was boiled under reflux in a 300 mL flask using a nickel(II) acetate catalyst (2.54 mg, 20 ppm Ni) which was added over 17 minutes. The reaction temperature ranged from about 60°-69° C. The percent conversion of TNPA to TNHA over time as determined by gas chromatography was as follows:

| Time (min.)[1] | % TNHA |
| --- | --- |
| 5 | 47.6 |
| 15 | 59.0 |
| 30 | 69.0 |
| 60 | 83.0 |
| 120 | 88.6 |

[1]Time after catalyst was fed.

The product was vacuum stripped to remove excess hexenes.

General Back-Displacement Procedure

The tri-n-hexylaluminum prepared in the IsomerizationDisplacement Process is subjected to a back-displacement with excess 1-olefin, preferably propylene under pressure in the range of 150 psig using added catalyst, in a mechanically stirred 300 cc carbon steel autoclave at ambient temperatures e.g. about 20°-22° C. for about 10 minutes. The propene from a cylinder was liquified and introduced into the autoclave through a feed line. The catalyst, preferably nickel(II) naphthenate, was introduced through an addition tube which was also used to introduce an isomerization inhibitor e.g. 1,5-cyclooctadiene or a lead catalyst poison e.g. lead carboxylate. Upon completion of the reaction, the autoclave was vented to remove excess propene and the reaction mixture was sampled and analyzed by gas chromatography.

EXAMPLE 11B

Tri-n-hexylaluminum product (48.3 grams) prepared in Example 11A was back-displaced with propylene (about 50 grams) using a Ni(II) naphthenate catalyst (2 mg, 20 ppm Ni) for 3 minutes after which 28 mg of Pb as lead carboxylate were added and the propene was vented. The reaction temperature was 25° C. The conversion of the TNHA as calculated from G. C. analysis of the product, and not including the loss of 1-hexene during propylene venting, was about 55% of the equilibrium conversion. The vacuum stripped $C_6$ olefin product (12.5 grams) by normalized G. C. analysis contained about 97.5% 1-hexene, 1.2% vinylidene and 1.3% internal hexenes. (The remaining TNPA solution was used in Example 12A.)

EXAMAPLE 12B

Tri-n-hexylaluminum product prepared in Example 12A was back-displaced with propylene (about 45 grams) using a Ni(II) naphthenate catalyst (22 ppm Ni) for 10 minutes after which 10.5 mg of Pb as lead carboxylate were added and the excess propylene was vented. The reaction temperature was about 25°–28° C. The conversion of the TNHA as calculated from G. C. analysis of the product was about 53% of the equilibrium conversion, excluding the loss of 1-hexene during propene venting. The vacuum stripped $C_6$ olefin product (9.7 grams) by normalized G. C. analysis contained about 97.0% 1-hexene, 1.6% vinylidene and 1.4% internal hexene. (The vinylidene was believed to be in the n-hexene feed for the isomerization/displacement reaction.)

EXAMPLE 13B

The tri-n-hexylaluminum product prepared in Example 13A was back-displaced with 1-octene (670 m mole) at a temperature of about 70° C. without any added catalyst for 8 minutes after which 5.6 mg of Pb as lead carboxylate were added. The conversion as estimated from G. C. analysis was about 61.5% or about 70% of the equilibrium conversion. The vacuum stripped $C_6$ olefin product (54.65 grams) by normalized G. C. analysis contained about 97.6% 1-hexene, 1% vinylidene and 1.4% internal hexenes. This example demonstrates that, at an elevated displacement temperature, the spent nickel catalyst from the isomerization/displacement reaction is effective to catalyze the back-displacement.

EXAMPLE 14B

A portion (4.3 g) of the tri-n-hexylaluminum product prepared in Example 14A was back-displaced with 1-octene (112 m mole) using a cobalt II naphthenate catalyst (0.7 mg, 10 ppm as Co) at a temperature of 22.8° to 23.5° C. for 60 minutes and then the temperature was raised to from 45° to 47° C. for sixty minutes. No catalyst poison or isomerization suppressants were added. The normalized G. C. analysis of the product for vinylidenes and internal hexenes over time was as follows:

| Time (min) | Temp °C. | % of Equilibrium Conversion | 1-hexene | i-hexenes | vinylidene[1] |
|---|---|---|---|---|---|
| 30 | 22.8 | 35.8 | 97.3 | 1.7 | 1.0 |
| 60 | 22.9 | 47.8 | 97.6 | 1.4 | 1.0 |
| +5 | 45.1 | 60.9 | 97.6 | 1.4 | 1.0 |
| 10 | 44.3 | 65.6 | 97.6 | 1.5 | 0.9 |
| 15 | 44.4 | 69.1 | 97.3 | 1.6 | 1.1 |
| 20 | 44.6 | 72.4 | 97.4 | 1.7 | 1.0 |
| 60 | 47.2 | 81.6 | 97.2 | 1.8 | 1.0 |

[1] Believed to be from a vinylidene impurity in the n-hexenes fed in Example 14A.

The results show that the cobalt(II) naphthenate catalyst was effective to catalyze the back-displacement reaction without causing any significant isomerization of the 1-hexene product.

EXAMPLE 15B

A 33.3 gram portion of tri-n-hexylaluminum product prepared according to Example 15A was back-displaced with propylene (125 grams) using a nickel(II) naphthenate catalyst (4 mg, 25 ppm Ni) for 10 minutes. A catalyst poison was not used but 12cc (about 10.6 grams) of 1,5-cyctooctadiene (COD) was added into the reaction mixture. The normalized G. C. analysis of the vacuum stripped product was 98.3% 1-hexene, 1% vinylidene and 0.7% internal hexenes. The example demonstrates that the COD was effective in suppressing isomerization of the product.

What is claimed is:

1. A process for making an alkyl aluminum compound from an internal olefin, said process comprising:
   (a) reacting (i) a linear internal olefin containing 4 to about 30 carbon atoms or a mixture of such internal olefins and (ii) a trialkyl aluminum which contains less than about 1.0 wt % of aluminum hydride impurity, the mole ratio of said linear internal olefins to said trialkyl aluminum being about 1–40/1, in the presence of a catalytic amount of a nickel-containing isomerization/displacement catalyst to cause isomerization of the internal olefinic double bond to form at least some linear 1-olefin and to cause the linear 1-olefin so-formed to displace alkyl groups from said trialkyl aluminum and form an alkyl aluminum compound wherein at least one of the alkyl groups bound to aluminum is a linear alkyl derived from said linear 1-olefin.

2. The process of claim 1 wherein said nickel catalyst is selected from nickel(II) salts, nickel(II) carboxylates, nickel(II) acetonates and nickel(0) complexes including mixtures thereof.

3. The process of claim 2 wherein said nickel catalyst is selected from nickel bis-1,5-cyclooctadiene, nickel acetate and nickel chloride.

4. The process of claim 1 wherein said nickel catalyst is stabilized by complexation with a trivalent phosphorus ligand.

5. The process of claim 1 wherein said trialkylaluminum is selected from trineohexylaluminum, triisobutylaluminum, tri-n-butylaluminum, triethylaluminum and tri-n-propylaluminum.

6. The process of claim 5 wherein said trialkyl aluminum is tri-n-propylaluminum.

7. The process of claim 1 wherein said catalyst is present in an amount of from about 0.01 to 5.0 mole percent of the trialkyl aluminum.

8. The process of claim 7 wherein said catalyst is present in an amount of from about 0.02 to 1.0 mole percent of the trialkyl aluminum.

9. The process of claim 1 wherein said linear internal olefin is an n-hexene.

10. The process of claim 1 wherein the alkyl groups of said trialkyl aluminum contain fewer carbon atoms than said linear internal olefin or olefins.

11. The process of claim 1 wherein said catalyst is mixed with said internal olefin or olefins prior to mixing with said trialkyl aluminum.

12. The process of claim 1 wherein said trialkyl aluminum contains less than about 0.1 wt % of aluminum hydride.

* * * * *